(12) United States Patent
Luk et al.

(10) Patent No.: US 6,553,807 B2
(45) Date of Patent: Apr. 29, 2003

(54) DISC DRIVE COMPONENT LEVEL SHOCK TESTER

(75) Inventors: Allan Kai Luk, Thornton, CO (US); Gary Edwin Bement, Frederick, CO (US); Jerome Frederick Griep, Longmont, CO (US); Frederick Paul Renken, Boulder, CO (US)

(73) Assignee: Seagate Technology LLC, Scotts Valley, CA (US)

( * ) Notice: Subject to any disclaimer, the term of this patent is extended or adjusted under 35 U.S.C. 154(b) by 0 days.

(21) Appl. No.: 09/894,639

(22) Filed: Jun. 27, 2001

(65) Prior Publication Data

US 2002/0035865 A1 Mar. 28, 2002

Related U.S. Application Data

(60) Provisional application No. 60/241,643, filed on Oct. 13, 2000.

(51) Int. Cl.[7] .................................................. G01M 7/00
(52) U.S. Cl. ........................................................ 73/12.09
(58) Field of Search ............................. 73/11.01, 12.01, 73/12.04, 12.09

(56) References Cited

U.S. PATENT DOCUMENTS

| 4,008,492 A | 2/1977 | Elsing ........................ 360/98 |
|---|---|---|
| 4,054,931 A | 10/1977 | Bolton et al. .................. 360/97 |
| 4,130,845 A | 12/1978 | Kulma ........................ 360/97 |
| 4,282,554 A | 8/1981 | Ho et al. ...................... 360/97 |
| 4,317,146 A | 2/1982 | Gervais ........................ 360/98 |
| 4,888,655 A | 12/1989 | Bonn ....................... 360/97.03 |
| 6,050,127 A | * 4/2000 | Rao et al. .................. 73/12.06 |
| 6,122,164 A | * 9/2000 | Liao et al. ................... 248/500 |
| 6,212,026 B1 | * 4/2001 | Ohmi et al. .................. 360/60 |

* cited by examiner

*Primary Examiner*—Max Noori
(74) *Attorney, Agent, or Firm*—Merchant & Gould P.C.

(57) ABSTRACT

A shock test apparatus for evaluating the shock performance of individual disc drive components includes a base portion and a top cover connected to the base portion to define an interior volume. First and second disc drive components are secured within the interior volume of the apparatus to engage one another in the absence of a shock event. A shock pulse generator includes an actuator for imparting a shock pulse to one of the disc drive components. A second shock pulse generator can be used to impart a shock pulse to the second disc drive component. Measurements are made of both the shock imparted to the disc drive components and the interaction between the first and second disc drive components during the shock event.

24 Claims, 6 Drawing Sheets

DISC DRIVE COMPONENT LEVEL SHOCK TESTER

RELATED APPLICATION

This application claims the benefit of U.S. Provisional Application 60/241,643, entitled A COMPONENT LEVEL PARTICLE SHOCK TESTER, filed Oct. 13, 2000.

FIELD OF THE INVENTION

The present invention relates generally to improving the ability of disc drives to withstand shock events. More particularly, the present invention relates to a system for analyzing the shock performance of individual disc drive components such as a suspension or a read/write head.

BACKGROUND OF THE INVENTION

The current breed of disc drives spin much faster and are more densely packed with data than prior drives. These speed and size increases require that the read/write heads fly very close to the surface of the disc platters (on the order of a micron). In light of these very low fly heights, the shock performance of a disc drive has taken on paramount importance. Specifically, disc drives must be able to survive large non-operating shocks which are likely to cause an impact between the head and the disc media.

Current disc drive "shock tests" utilize a drop test where an entire drive is dropped from a predetermined height at different predetermined angles. The drop test attempts to simulate the types of shocks that will be experienced by disc drives under real world conditions. However, the drop test provides only limited information about the shock performance of a disc drive. Indeed, drop tests are more of a "survivability" test where the disc drive is analyzed to see if it can still pass a battery of read/write and seek commands following the drop test.

It is possible to combine disc drive drop tests with real-time analysis of the disc by modifying portions of the disc drive. For example, a top cover of the disc drive may be modified to include an evacuation line for applying a suction to the interior of the drive. In this manner, the modified disc drive could be connected to a particle counter during the drop test to measure the amount of particles generated during the test. However, even such limited whole-drive shock testing is subject to a number of drawbacks.

Specifically, whole-drive shock testing is extremely inefficient due to the requirement that an entire disc drive must be constructed before any testing can be done. There is always pressure to reduce the time-to-market for new disc drives, and thus it is imperative to begin testing the new technology as soon as possible. Long delays may be encountered if shock-related problems are discovered only after production begins on a new disc drive line. Thus, it would be desirable to be able to perform shock tests on individual disc drive components, as opposed to waiting until the components are integrated within a fully functional disc drive.

A further drawback to whole-drive shock testing is that it is difficult to isolate the performance of a single component when the entire drive is subjected to shock testing. That is, due to the large number of interrelated components within a disc drive, it is difficult to measure the shock performance of a single component (e.g., a read/write head or a suspension) since a disc drive may experience a failure for reasons that are not related to the tested components.

Additionally, it is difficult to obtain accurate comparative testing using whole-drive shock testing. Comparative testing comprises, for example, installing two different suspensions or read/write heads within a disc drive and then performing drop tests on the drive to determine which suspension performed better under the shock load. However, it is not a simple matter to build two complete disc drives with different components in order to test the components. Furthermore, as noted above, it is difficult to isolate the performance of a single component when drop testing an entire drive, and this further complicates the effort to perform comparative testing.

In addition to the inefficiencies associated with whole-drive shock testing, prior art drop tests also provide limited value since the test results are not highly repeatable. Specifically, due to the nature of the drop test, it is possible for random events to impact the test results and thereby impair the ability to obtain consistent test results. Furthermore, due to drive yield issues, minor variations between different disc drives also limits the repeatability of shock test results for the above noted reasons (i.e., the same interrelation between the drive components which makes it difficult to isolate the performance of a single component also makes it difficult to obtain highly repeatable test results when two different drives are not identical). Thus, two different disc drives may fail a drop test for two different reasons.

In sum, prior art whole-drive testing is not efficient since it can not be performed until after the disc drive design has been finalized and manufacture of the drives has begun. It would be desirable to perform shock tests on individual drive components earlier in the design effort before time and money is expended to build an entire disc drive. Additionally, current whole drive drop tests do not provide an opportunity to accurately study the shock performance of individual disc drive components. Specifically, current drop tests do not allow researchers to accurately compare two different components (e.g., the mechanical dynamics and particle-shedding nature of two different suspension designs) to determine the better design with respect to shock performance.

The present invention provides a solution to these and other problems, and offers other advantages over the prior art.

SUMMARY OF THE INVENTION

In accordance with one preferred embodiment of the present invention, a shock test apparatus is provided for evaluating the shock performance of individual disc drive components. The apparatus includes a base portion and a top cover connected to the base portion to define an interior volume. First and second disc drive components are detachably secured within the interior volume of the apparatus so that the first disc drive component engages the second disc drive component in the absence of a shock event. In this manner, the apparatus simulates a relevant portion of a disc drive when the drive is at rest. A shock pulse generator includes an actuator extending into the interior volume of the apparatus for imparting a shock pulse to the first disc drive component, thereby creating a dynamic interaction or impact between the first and second disc drive components. A second shock pulse generator may also be connected to impart a shock pulse to the second disc drive component to aid in simulating a variety of real world shocks experienced by a disc drive. In one preferred embodiment, the first disc drive component is a head suspension assembly, while the second disc drive component is a media disc (to simulate a Contact Start/Stop disc drive) or a ramp fixture (to simulate a Load/Unload disc drive).

The present invention further includes a system for evaluating the shock performance of individual disc drive components without having to first build a disc drive. The system includes an enclosure having a base portion and a top cover connected to define an interior volume. First and second disc drive components are detachably secured within the interior volume of the enclosure so that the first disc drive component engages the second disc drive component in the absence of a shock event. The system includes a shock pulse generator having an actuator extending into the interior volume of the enclosure to impart a shock pulse to the first disc drive component, thereby creating a dynamic interaction or impact between the first and second disc drive components. The system further includes means for measuring the shock pulse imparted to the first disc drive component, as well as means for measuring the dynamic interaction between the first and second disc drive components. In one embodiment, the system includes a second shock pulse generator having an actuator extending into the interior volume of the enclosure to impart a shock pulse to the second disc drive component as well as means for measuring the shock pulse imparted to the second disc drive component. In a further embodiment, the means for measuring the shock pulses include accelerometers attached to the first and second disc drive components or the actuators used to shock those components, while the means for measuring the dynamic interaction of the two disc drive components includes one of a laser Doppler vibrometer, a particle counter, a particle trap, a sample collection disc, and an acoustical emission sensor.

These and various other features as well as advantages which characterize the present invention will be apparent from a reading of the following detailed description and a review of the associated drawings.

DETAILED DESCRIPTION OF THE PREFERRED EMBODIMENTS

Figure 1:
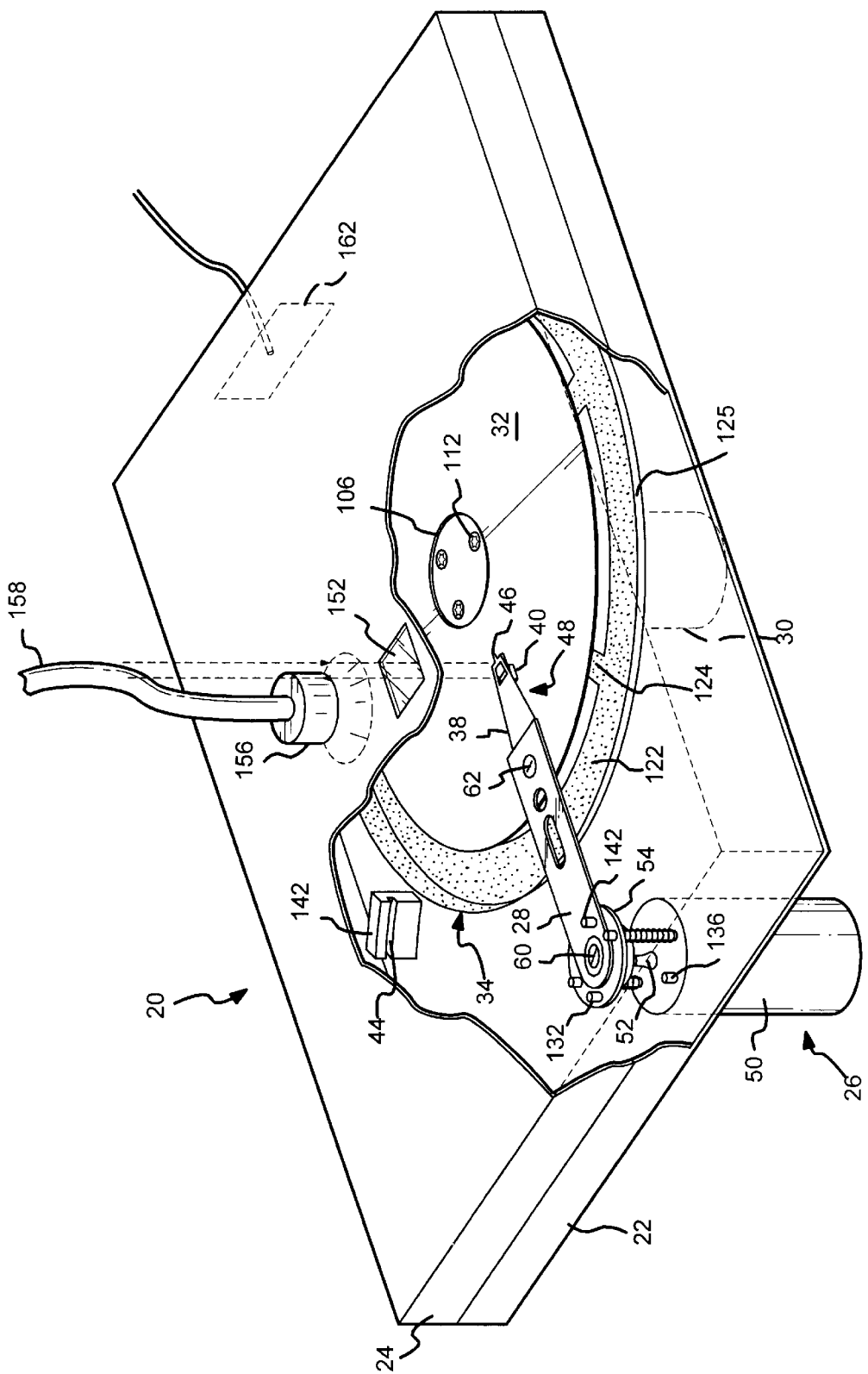
FIG. 1 is an isometric view of a component level shock test apparatus in accordance with a preferred embodiment of the present invention.

FIG. 1 illustrates a preferred embodiment of a component level shock test apparatus 20 of the present invention. The shock test apparatus 20 includes a base portion 22 and a top cover 24 that define an interior volume when secured together. The base portion 22 and top cover 24 are preferably formed from a metal such as aluminum. A first shock pulse generator or "shaker" 26 extends through an opening formed in the base portion 22 and supports a disc drive actuator arm within the interior volume of the apparatus 20 as shown in FIG. 1. A second shock pulse generator 30 extends through a second opening formed in the base portion 22 and supports both a media disc 32 and a sample collection disc 34 in the interior volume of the apparatus 20.

In one preferred embodiment shown in FIG. 1, the base portion 22 is supported by the generators 26 and 30 so that the entire apparatus may be supported by placing the bottom surface of the shock pulse generators 26 and 30 on a table or other support. Alternatively, the base portion 22 may include leg supports (not shown) so that the bottom surfaces of shock pulse generators 26 and 30 extend down from the base portion 22 but do not engage the table or other support which engages the legs.

Within the interior of the apparatus 20, a suspension 38 connects a distal end of the actuator arm 28 to a slider 40 of a read/write head. An air bearing surface (not shown) of the slider 40 rests on a top surface of the media disc 32 and simulates a non-operating condition of a Contact Start/Stop ("CSS") disc drive. It is from this starting position that the shock test is performed as described in detail below.

FIG. 1 also illustrates a ramp 42 secured to the base portion 22. The ramp 42 is positioned along a radial arc of the suspension 38 and slider 40 and is located beyond the circumference of both the media disc 32 and the sample collection disc 34. The ramp includes a groove or slot 44 for receiving a finger 46 that extends outward and away from the slider 40 at the distal end of the suspension 38. The finger 46 thus supports the weight of the suspension 38 and slider 40 while preventing contact between the slider 40 and the ramp 42. Using the ramp 42 to "park" the suspension 38 and slider 40 in this manner allows the test apparatus 20 to simulate the non-operating condition of a Load/Unload disc drive.

Figure 7:
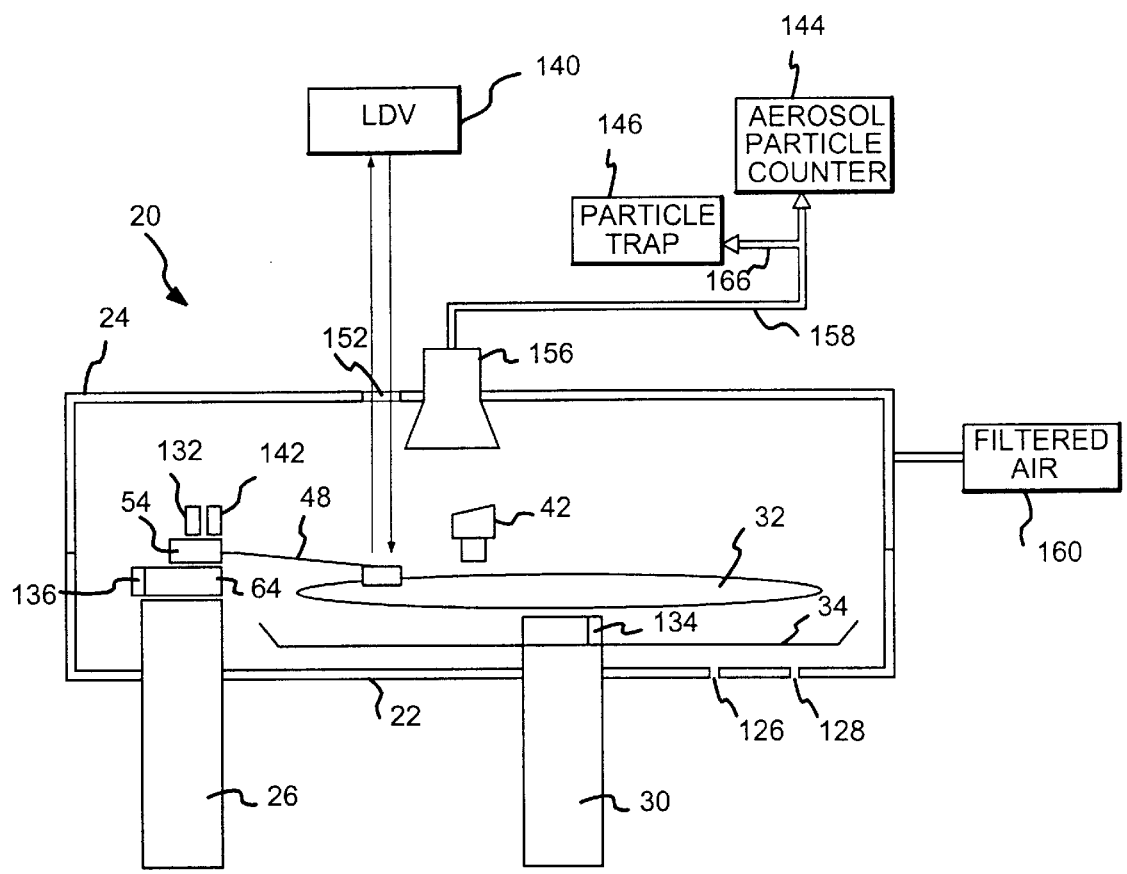
FIG. 7 is a schematic view of the shock test apparatus shown in FIG. 1 together with testing and analysis equipment used to evaluate the results of the shock test conducted by the shock test apparatus.

The basic operation of the shock test apparatus 20 is explained with reference to FIG. 1 as well as the schematic view shown in FIG. 7. While FIGS. 1 and 7 depict a simulation of a CSS disc drive (because the slider 40 is in contact with the disc 32), it is understood that component shock testing for Load/Unload disc drive components could be conducted in the same manner as that shown in FIGS. 1 and 7 provided that the suspension 38 is "parked" in the ramp 42 at the beginning of the test.

The shock test apparatus 20 utilizes the shock pulse generators 26 and 30 to simulate a shock event experienced by an actual disc drive. The discrete shock pulse generators 30 and 26 apply separate shocks to the media disc 32 and the assembly of the suspension 38 and the slider 40 (referred to herein as the "head suspension assembly" or "HSA" 48). The respective shock pulse generators 26 and 30 are preferably controlled by a computer or other control station (not shown) to provide specific shocks that closely imitate real world non-operating shocks (e.g., dropping a disc drive). The two shock pulse generators 26 and 30 are shown in greater detail in FIGS. 4–6.

Figure 4:
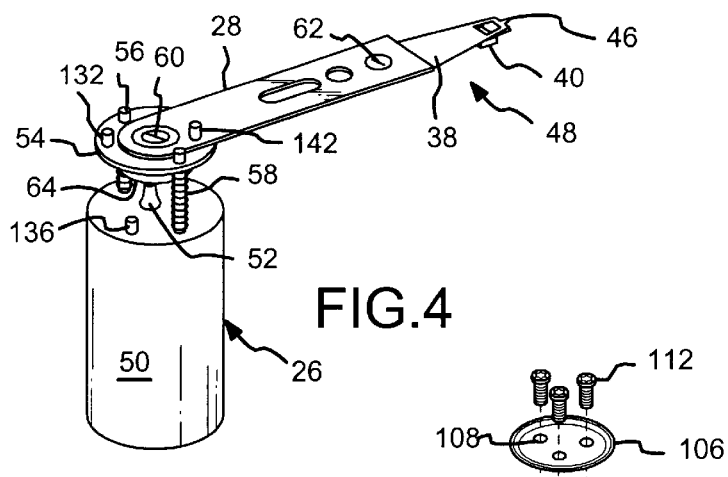
FIG. 4 is an enlarged isometric view of a first shock pulse generator shown in FIG. 1. The first shock pulse generator is connected to an actuator arm for applying a shock to the head/suspension assembly attached to the actuator arm.

FIG. 4 illustrates the first shock pulse generator 26 and its attachment to the actuator arm 28. The shock pulse generator 26 comprises a cylindrical body 50 that is fixed relative to the base portion 22 of the apparatus 20 (FIG. 1). An actuator 52 extends vertically from a top surface of the cylindrical body 50 to provide the shock pulse, as described below. A circular platform 54 is suspended vertically above the actuator 52 by two posts 56 which extend through two diametrically opposed openings formed in the circular platform 54. The posts 56 are secured to the top surface of the shock pulse generator 26 so that the circular platform 54 is centered over the actuator 52. While the posts 56 hold the platform 54 at a precisely defined level within the apparatus 20, it is desirable to allow a slight amount of flex in the posts 56 to prevent them from failing prematurely after experiencing repeated shock pulses from the actuator 52. Indeed, one preferred embodiment shown in FIG. 4 utilizes springs 58 wrapped about each of the posts 56, and extending between the bottom surface of the platform 54 and the top surface of the shock pulse generator 26, to dampen any movement of the platform 54. The springs 58 thus serve to dampen vibrations in the actuator arm 28 and the HSA 48 following the application of a shock pulse by the actuator 52.

FIG. 4 further illustrates the connection of a proximal end of the actuator arm 28 to the circular platform 54. While a screw 60 is shown connecting the actuator arm 28 to the platform 54 in FIG. 4, it is understood that any other suitable fastener may be used to releasably secure the actuator arm 28. The use of a fastener such as the screw 60 allows for the use of different actuator arms in the testing apparatus 20. In this manner, the shock performance of various actuator arms 28 may be tested. A second fastener 62 connects the distal end of the actuator arm 28 to a proximal end of the suspension 38. As noted above, the use of a screw 62 or similar fastener allows for the easy replacement of the suspension 38 so that different HSAs may be tested within the apparatus 20.

A programmer disc 64 is preferably attached to a bottom surface of the circular platform 54 so that the programmer disc 64 is also centered above the actuator 52. The programmer disc 64 is preferably formed from an elastomeric material and is used to alter the duration of the shock applied by the actuator 52 to the HSA 48. That is, while the shock pulse generator 26 controls the amount of force applied to the actuator 52, different programmer discs 64 can be used to alter the type of shock that is applied to the platform 54 and thus to the HSA 48. In one preferred embodiment, the elastomeric disc 64 is attached to the bottom of the platform 54 by an adhesive so that the disc 64 can be easily replaced with other discs to simulate different shock events. However, alternative means (such as a retaining bracket secured to the bottom platform 54) may be used to secure the programmer disc 64 to the platform 54 so that a plurality of different discs 64 may be used interchangeably. The use of elastomeric discs, in general, to alter or dampen shock pulses is well known to those skilled in the art and will not be described further herein.

Figure 5:
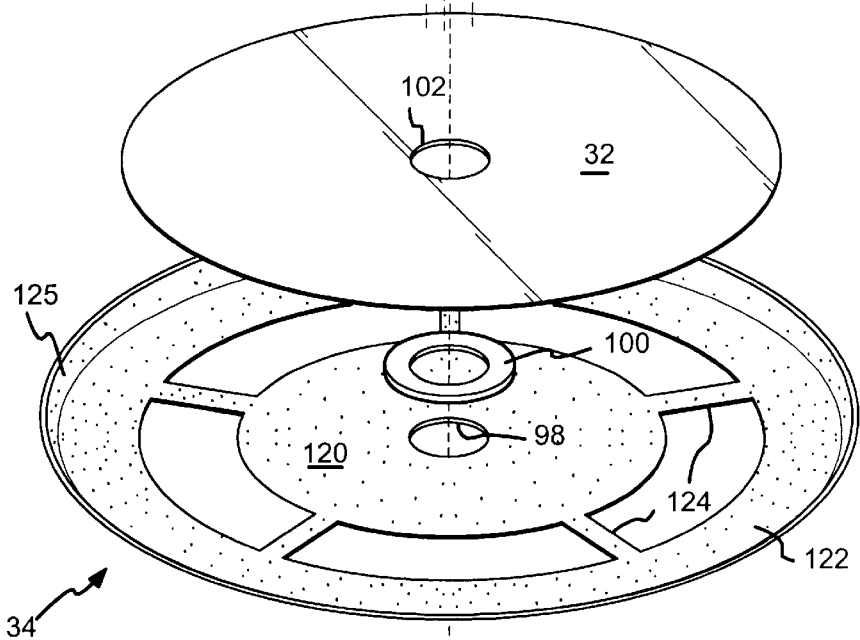
FIG. 5 is an enlarged, exploded view of a second shock pulse generator attached to a media disc and a sample collection disc as shown in FIG. 1.
Figure 5:
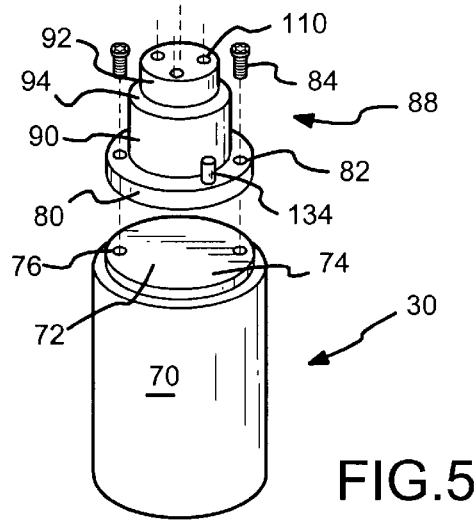

FIG. 5 illustrates the second shock pulse generator 30 and its attachment to both the media disc 32 as well as the sample collection disc 34. Specifically, the second shock pulse generator 30 also includes an outer cylindrical housing 70 (fixed in relation to the base portion 22 of the shock test apparatus 20) as well as an actuator portion 72 which moves vertically with respect to the cylinder 70. The actuator portion 72 is of a much larger diameter than the actuator 52 found on the first shock pulse generator 26 and includes a contact surface 74 with threaded holes 76 for receiving a hub base 80 as described below.

The hub base 80 is circular in shape having a diameter that is no larger than, and is preferably smaller than, the diameter of the actuator portion 72 of the shock pulse generator 30. The hub base 80 includes holes 82 defined therein which match the threaded holes 76 in the contract surface 74 of the actuator portion 72. Screws 84 are preferably used to secure the hub base 80 to the contact surface 74 of the actuator portion 72, although one skilled in the art may substitute alternative connection means or may form the hub base 80 integrally with the actuator portion 72.

FIG. 5 further illustrates a cylindrical hub 88 connected to the hub base 80 so that the hub 88 can rotate (about a vertical axis) relative to the fixed hub base 80. The hub 88 includes a lower cylindrical section 90, having a relatively large diameter, and an upper cylindrical section 92 having a smaller diameter. A horizontal flange 94 is defined at the intersection of the two cylindrical sections 90 and 92 and provides a base for supporting the sample collection disc 34 and the media disc 32. In this manner, the hub 88 simulates the type of hub used within conventional disc drives, although the apparatus 20 preferably does not include a spin motor for rotating the hub 88. Rather, the hub 88 is rotated manually between consecutive shock tests, as described below.

The sample collection disc 34 includes a center opening 98 having a diameter that is slightly larger than the diameter of the upper cylindrical section 92 of the hub 88. The opening 98 is press fit over the upper cylindrical section 92 of the hub 88 so that a bottom surface of the sample collection disc 34 rests upon the flange 94 of the hub 88. A spacer disc 100 is then fit over the upper section 92 of the hub to rest upon an upper surface of the sample collection disc 34 as shown in FIG. 5. Next, a center opening 102 of the media disc 32 is fit over the upper section 92 of the hub 88 so that a bottom surface of the media disc 32 is supported by a top surface of the spacer disc 100. In this manner, the spacer disc 100 provides a predetermined spacing between the media disc 32 and the sample collection disc 34, while the flange 94 supports both discs on the rotatable hub 88.

A clamp ring 106 is preferably used to secure the discs 32 and 34 against the flange 94 during the testing procedure. The clamp ring 106 has an outer periphery for contacting the top surface of the media disc 32 and includes a plurality of holes 108 arrayed in a pattern for alignment with a plurality of threaded holes 110 formed in a top surface of the hub 88. Screws or other threaded fasteners 112 are then used to secure the clamp ring 106 to the hub 88 and thereby secure the discs 32, 34 and 100 between the clamp ring 106 and the flange 94. The detachable clamp ring 106 allows for quick and easy replacement of the media disc 32 as well as the sample collection disc 34.

In a preferred embodiment, both the media disc 32 and the sample collection disc 34 fit snugly against the outer perimeter of the upper section 92 of the hub 88 so that both discs 32 and 34 rotate together with the hub 88. Alternatively, the center opening 98 of the sample collection disc 34 may be slightly larger than the outer perimeter of the hub to define a relatively loose fit with the hub. Such a loose fit would allow the disc 34 to be rotated relative to the hub 88 between consecutive test procedure and would also ease removal of the disc 34 from the hub 88 at the completion of the test.

Once the discs 32 and 34 are secured to the hub 88 as described above, the actuator portion 72 of the shock pulse generator 30 can be manipulated as desired to shock or vibrate the hub 88 and thus the media disc 32 during the shock test. The close fit between the media disc 32 As and the hub 88 simulates the conditions found in a disc stack within a typical disc drive. Furthermore, as noted above, the shock pulse generator 30 is controlled independently of the shock pulse generator 26 attached to the actuator arm 28 to allow for maximum flexibility in simulating different types of shock events.

Figure 6:
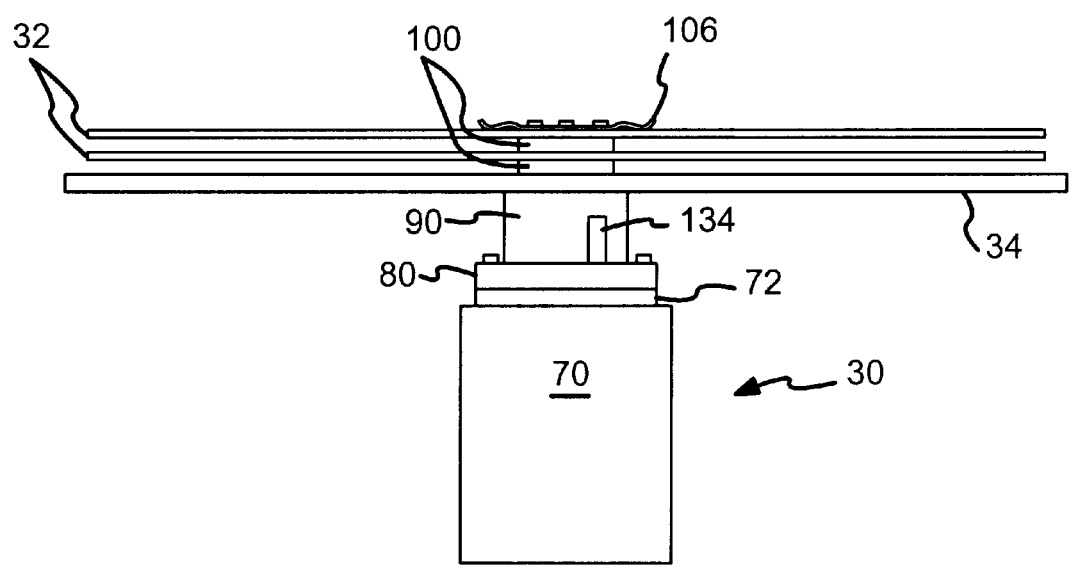
FIG. 6 is a side elevational view of the second shock pulse generator shown in FIG. 5 illustrating a second media disc stacked above the first media disc shown in FIG. 5.

While FIG. 5 shows only a single media disc 32 attached to the hub 88 of the test apparatus 20, those skilled in the art understand that additional media discs may be attached to the hub 88 by constructing a hub having an extended upper section 92 and using additional spacer discs 100 to separate the media discs 32. FIG. 6 illustrates such an alternative embodiment where two media discs 32 are stacked on the hub 88 above the sample collection disc 34. The ability to perform shock tests with the same number of discs that are to be used in the disc drive itself is helpful in simulating the shock performance of an actual disc stack within a disc drive.

Details of one preferred embodiment of the sample collection disc 34 are best shown in FIG. 5. The sample collection disc 34 preferably has a larger diameter than that of the media disc 32. For example, in one preferred embodiment, the diameter of the media disc in 3.5 inches while the diameter of the sample collection disc 34 is approximately 3.8 inches. While alternative designs of the disc 34 (e.g., a solid disc) fall within the scope of the present invention, the disc 34 is preferably segmented into two concentric discs (120 and 122) connected by spokes 124. The inner disc 120 of the sample collection disc 34 includes the opening 98 which fits over the hub 88, while the outer disc 122 is positioned underneath the periphery of the media disc 32 and extends slightly beyond the periphery of the media disc 32 due to the larger diameter of the overall sample collection disc 34. In the preferred embodiment shown in FIG. 5, an outer periphery 125 of the outer disc 122 is bent upward toward the media disc 32 to enhance the particle collection process as described below.

Figure 2:
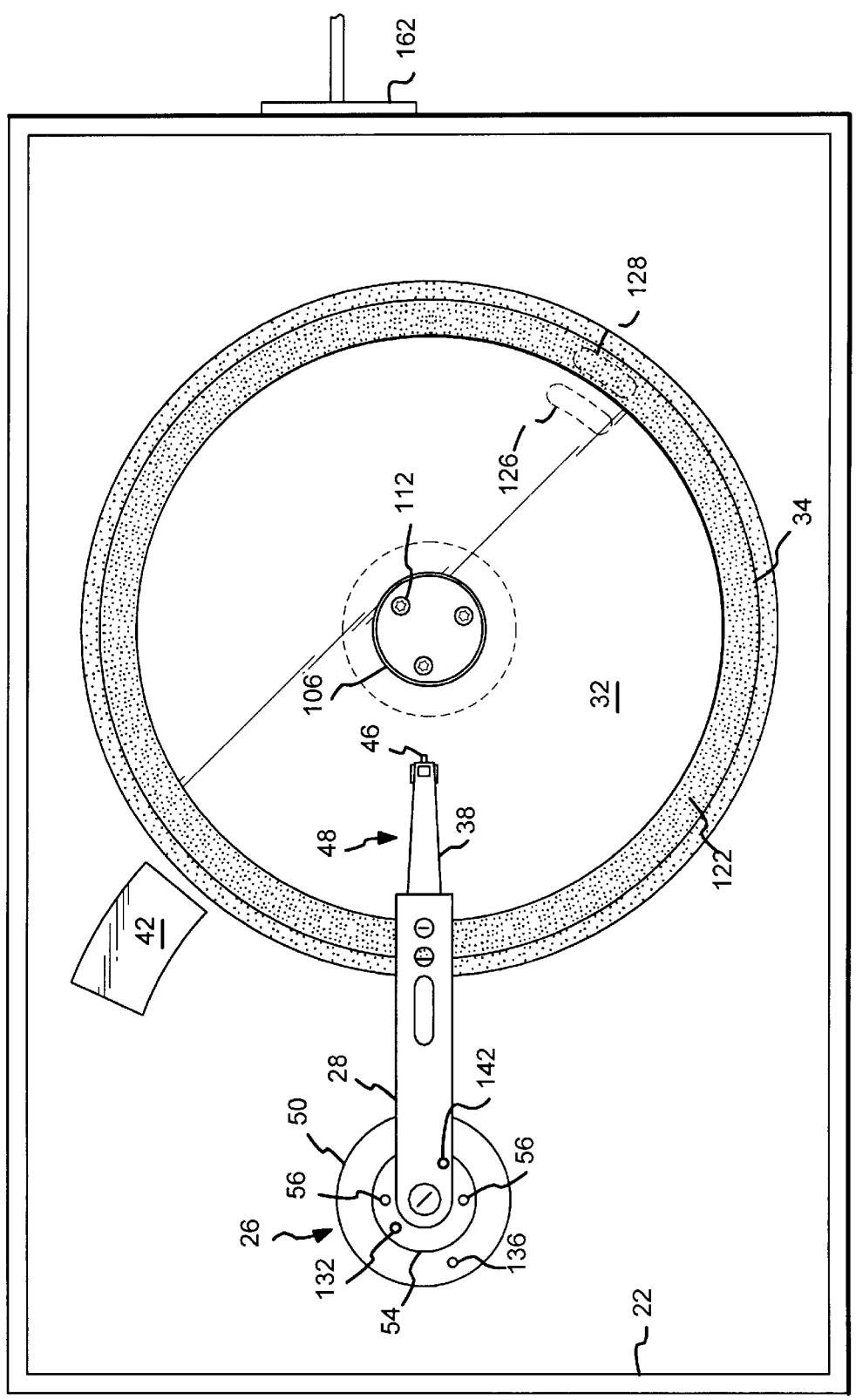
FIG. 2 is a top view of the shock test apparatus shown in FIG. 1 shown with a top cover removed.
Figure 3:
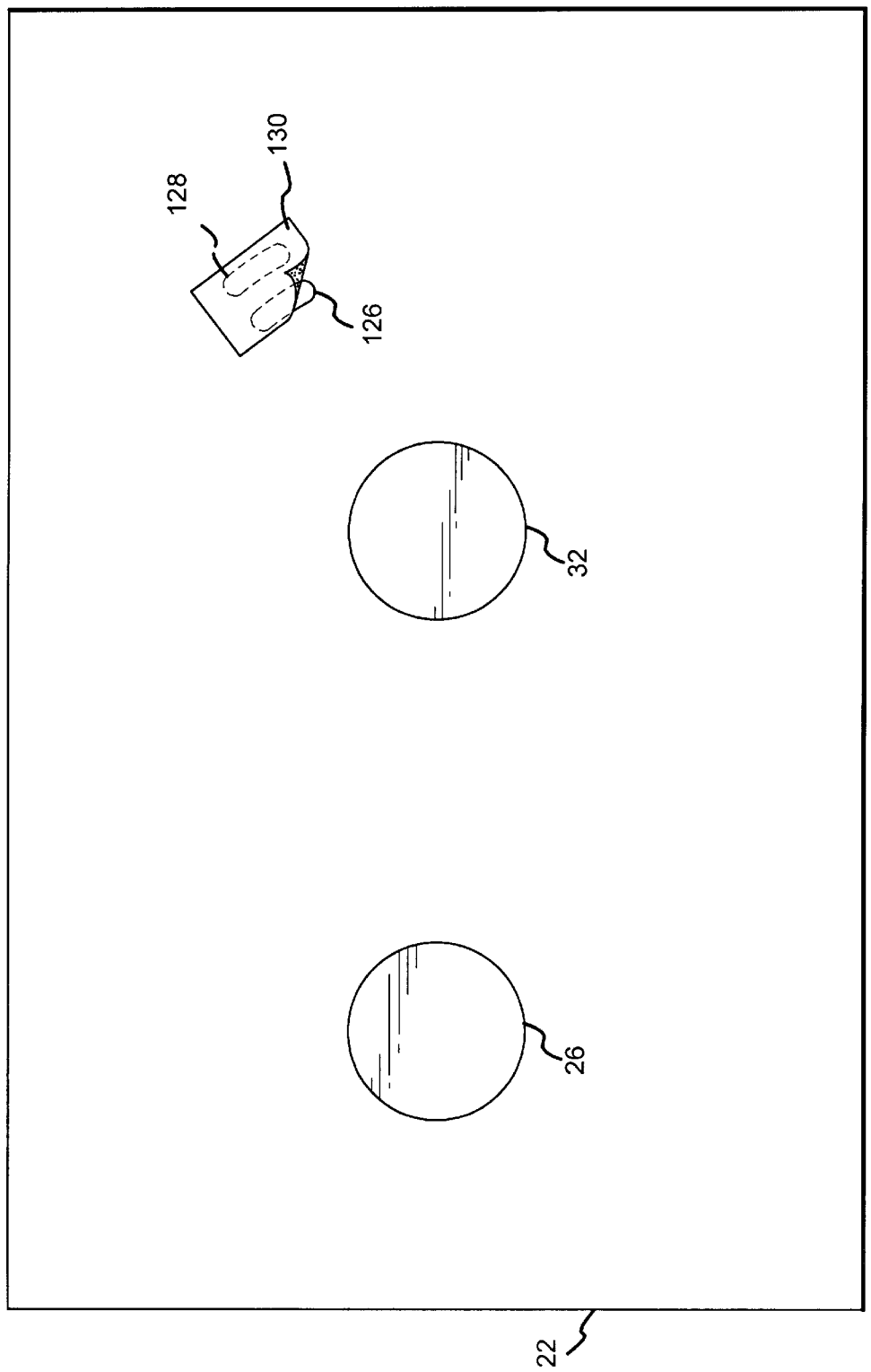
FIG. 3 is a bottom view of the shock test apparatus shown in FIG. 1.

The spokes 124 of the sample collection disc provide access to the bottom surface of the media disc 32 from an opening or access port 126 (FIG. 3) formed in the base portion 22 of the apparatus 20. The access port 126 allows a sterile probe (e.g., a cotton swab) to be inserted into the interior of the apparatus 20 between adjacent spokes 124 to rotate the media disc 32 and thus the hub 88. In the event that the sample collection disc 34 fits snugly about the upper section 92 of the hub 88, the disc 34 will turn with the hub 88 and the media disc 32. However, the primary reason for utilizing the spoked design of the sample collection disc 34 is to allow the media disc 32 and the hub 88 to be rotated independently of the sample collection disc 34. Thus, in those embodiments where the sample collection disc 34 is not snugly fit to the hub 88, a probe may be inserted through the access port 126 to rotate the media disc 32 (and hub 88) while simultaneously contacting one of the spokes 124 to prevent the sample collection disc 34 from rotating. Alternatively, a second opening or access port 128 (FIG. 3) may be formed in the base portion 22 to provide access to the bottom surface of the sample collection disc 34. The second access port 128 is preferably formed adjacent the first access port 126 and, while both access ports are preferably arc-shaped to allow an inserted probe to be moved along an arcuate path, the second access port 128 is positioned a greater radial distance from the center of the hub 88 (see FIG. 2). In this manner, a probe inserted through the second access port 128 can be used to contact the outer disc 122 of the sample collection disc 34 to rotate the sample collection disc 34 without necessarily rotating the hub 88 and the attached media disc 32. The purpose of the sample collection disc 34 is described in greater detail below. However, because the apparatus 20 is preferably sealed against contaminants during the course of the shock tests, both of the access ports 126 and 128 are preferably sealed by an adhesive cover 130 (FIG. 3) during the test procedure. The cover 130 preferably utilizes an adhesive that allows for repeated removal and reapplication of the cover 130 to the base portion 22 of the apparatus 20, thereby allowing an investigator to repeatedly insert probes within the access ports 126 and 128 to rotate the discs 32 and 34 during the test procedure.

As described above, the apparatus 20 includes a controller (not shown) used to vary both the sequence and the intensity of the shock pulses provided by the two shock pulse generators 26 and 30. Additionally, by varying the type of material and the thickness of the programmer disc 64, one can alter the duration of the shock experienced by the HSA 48. This flexibility in adjusting the sequence, duration and severity of the shocks delivered to both the actuator arm 28 (and the attached HSA 48) as well as to the media disc 32 allows the apparatus 20 to mimic a wider variety of shock conditions than prior art drop testers. Additionally, the apparatus 20 allows for shock tests of individual disc drive components prior to assembly of a completed disc drive. The types of components that may be tested within the apparatus include sliders 40, a suspensions 38, media discs 32, as well as more esoteric changes to a component such as a new magnetic coating or polishing technique for the surface of the disc 32.

In addition to allowing the early testing of disc drive components, the apparatus 20 also improves the accuracy and repeatability of prior art shock testing by employing a variety of analysis equipment and testing methods that were not possible with prior whole-drive shock tests.

Preferred embodiments of the analysis equipment and testing methods used with the apparatus 20 are shown both in FIG. 1 as well as the schematic illustration of a test system shown in FIG. 7. However, those skilled in the art will understand that additional test equipment may be successfully used with the shock test apparatus 20 of the present invention. Additionally, while the following analysis describes testing a CSS disc drive, it is understood that the testing equipment and process is similar to that used for testing a Load/Unload drive.

The apparatus 20 includes a number of analysis tools used to provide objective measures of the shock performance of the tested components. Before describing the different test equipment used to analyze the shock performance of the disc drive components, it is important to note the equipment that is used to monitor the shock pulses that are imparted to the disc drive components. Due to the use of separate shock pulse generators 26 and 30, it is desirable to measure the actual shock forces delivered to each of the actuator arm 28 and the media disc 32 by the respective generators (i.e., measure the amplitude, frequency, duration, etc. of the shock). Toward that end, an accelerometer 132 is fixed to the circular platform 54 adjacent the proximal end of the actuator arm 28, as shown in FIG. 4. The accelerometer 132 measures the instantaneous acceleration of the actuator arm 28 and the HSA 48 during the shock event. A second accelerometer 134 is preferably attached to the hub base 80 (FIG. 5) to measure the shock applied to the media disc or discs 32. In one preferred embodiment, a third accelerometer 136 may be attached to one of the shock pulse generators (e.g., the generator 26 in FIGS. 1 and 4) or to any other portion of the apparatus 20. This additional accelerometer 136 can then be used to measure any acceleration experienced by the test apparatus 20 itself, and thereby provide a more accurate measurement of the relative shock applied by the apparatus 20 to each of the HSA 48 and the media disc 32.

The accelerometers 132, 134 and 136 are each preferably attached to a computer (not shown) for collection of the acceleration data for each test run. The acceleration data is then stored in the computer memory together with the test data from a variety of instruments used to measure the shock performance of the drive components. This combination of accelerometers provides detailed information regarding the shock forces experienced by each of the disc drive components within the apparatus and thus helps to ensure that repeatable test results are obtained. This represents an improvement over prior art whole-drive testing where an accelerometer was typically placed on the housing of the disc drive (to measure the overall shock value experienced by the drive) but not on the individual components within the drive.

In addition to the accelerometers for monitoring the applied shock forces, a variety of analysis equipment is preferably used with the apparatus 20 for monitoring the effects of the shock pulses on the disc drive components. The test instruments used with the apparatus 20 provide a number of measurements which, when taken together, define the "shock performance" of the tested components. For example, different test instruments can be used to determine dynamic motion of the HSA 48 (e.g., how high the slider 40 lifts off the surface of the disc 32 as well as the number of times the slider "slaps" the disc surface), the resonance modes of the HSA 48, and the level of particle shedding which occurs when the slider 40 impacts the surface of the disc 32 during a shock event.

FIGS. 1 and 7 best illustrate the test instruments that are preferably used with the apparatus 20. These preferred test instruments include, but are not limited to, the following: a laser Doppler vibrometer ("LDV") 140, an acoustical emission sensor 142, a particle counter 144, and a particle trap 146 separate from the particle counter 144. Additionally, these instruments are supplemented by the use of carbon tape 150 (FIG. 5) on the sample collection disc 34 to capture particles that are not otherwise collected by the particle counter 144 and particle trap 146. Furthermore, traditional analysis techniques such as a microscopic analysis of the surface of the media disc 32 may also be employed at the conclusion of the shock test. These instruments are described in greater detail below.

The LDV 140 uses one or more laser beams (and the well known Doppler principle) to determine the relative speed of an object moving toward or away from the LDV. In the present invention, the LDV 140 is positioned directly above an opening formed in the top cover 24 of the apparatus 20 which, in turn, is positioned over the distal end of the HSA 48. A pane of antireflective glass 152 is set within the opening to allow the laser light from the LDV to pass unobstructed (i.e., without any loss of signal) through the opening as shown in FIG. 7. In this manner, the LDV 140 can measure the relative speed of the HSA 48 without contaminating the interior of the apparatus 20.

In the preferred embodiment, a dual-beam LDV 140 is used to measure both the motion of the HSA 48 as well as the motion of the surface of the media disc 32. In this manner, the LDV 140 can be used to analyze the motion of the slider 40 relative to the disc surface and thereby provide information such as the lift-off height of the head over the surface of the disc 32 as well as the number of "head slaps" which occurred during the shock test. This information is again passed to a computer (not shown) or other recording device together with the information from the accelerometers 132–136 which define the nature and intensity of the shock pulse.

The acoustical emission sensor 142 is preferably mounted on the actuator arm 28 leading to the HSA 48, although it may be mounted anywhere within the apparatus 20 where it will receive a clear acoustical signal. The acoustical emission sensor 142 essentially comprises a high frequency microphone that is tuned to listen to the bending motion of the HSA 48. The acoustical emission sensor 142 is preferably connected to a computer (not shown) to record the data from the sensor 142 together with the data from the accelerometers and the LDV 140. The sensitivity of the acoustical emission sensor 142 allows an investigator to distinguish the torsion, bending and sway modes of the HSA 48 during a shock event. Additionally, like the LDV 140, the acoustical emission sensor 142 can also be used to determine the number of "head slaps" that occur during a shock event. Thus, the acoustical emission sensor 142 provides important information regarding the dynamic performance of the HSA 48 that allows designers to improve the overall shock performance of the HSA 48.

While the LDV 140 and the acoustical emission sensor 142 are used to analyze the motion of the HSA 48 and the surface of the disc 32, the present invention utilizes a particle counter 144 to measure the amount of particles or debris that is generated during a shock event. The particle counter 144 includes a probe or sniffer 156 which extends through an opening formed in the top cover 24 of the apparatus 20. The sniffer 156 is connected to the particle counter 144 by a segment of electrically conductive tubing 158 (e.g., stainless steel tubing). The particle counter 144 includes a vacuum source for pulling particles upward (against the force of gravity) and through the tubing 158 for analysis within the particle counter. A source of filtered air 160 (FIG. 7) is preferably supplied to the interior of the apparatus 20 to prevent a complete vacuum from forming within the apparatus 20 and thereby assist in drawing the particles upward toward the sniffer 156. FIG. 1 illustrates a single source 160 of filtered air connected to a port 162 in the top cover 24 of the apparatus. However, one skilled in the art may employ more than one source of filtered air or may operate the apparatus 20 without a filtered air source provided that the particle counter does not create a complete vacuum within the interior of the apparatus 20. Additionally, because the particles generated during a shock event are typically metallic in nature (e.g., portions of the disc surface or the coatings applied to the surface of the disc 32), the conductive tubing 158 is preferably electrically grounded to prevent a static charge from building up within the tubing 158 and thereby ensnaring the particles before they can reach the particle counter 144.

The particle counter 144 is used to count the number of the particles generated during the shock test. The number of particles generated during a shock event provides a valuable representation of the shock performance and this information is stored in the computer (not shown) which is preferably connected to the particle counter 144.

While the particle counter 144 can also be used to measure the size of the particles generated during the test, it is preferable to connect a separate particle trap 146 in parallel with the particle counter 144. In the present invention, the particle trap 146 is connected to the conductive tubing segment 158 by a second segment of conductive tubing 166 as shown in FIG. 7. The use of a separate trap 146 allows for post-test analysis of the particles (e.g., analysis with a scanning electron microscope) and often provides a more accurate measure of particle size than can be obtained by the internal sensors of a particle counter. Since the present invention preferably utilizes conventional particle counter and particle traps that are well known to those skilled in the art, no further explanation of the operation of these devices is required.

In addition to the particle counter 144 and the trap 146, the present invention utilizes the above described sample collection disc 34 covered with carbon tape 150 to collect particles that are not other wise sucked through the sniffer 156 attached to the particle counter 144. Specifically, depending on the force of the vacuum supplied by the particle counter 144, as well as the size of the particles generated during the shock event, it is likely that some particles will fall down below the media disc 32 during the shock test. These particles are thus likely to impact the upper surface of the sample collection disc 34 where they will stick to the carbon tape that is applied to the disc 34. Specifically, the stray particles are most likely to impact the outer disc region 122 as well as the outer periphery 125 which is bent upward toward the media disc 32. However, due to the possibility that wind currents within the interior of the apparatus 20 (such as those generated by the vacuum source of the particle counter 144 and the filtered air source 160) may push the particles underneath the media disc 32, carbon tape is preferably affixed to both the spokes 124 and the inner disc 120 as well as the outer disc 122 and the periphery 125. Furthermore, if the actuator arm 28 is modified (not shown) to include a HSA 48 positioned beneath the media disc 32 (i.e., for holding a slider 40 against the bottom surface of the media disc 32), it is highly likely that a majority of the particles generated by an impact on the bottom surface of the disc 32 would not be collected by the sniffer 156. Rather, these particles would likely filter down and settle on the carbon tape 150 of the sample collection disc 34. Indeed, if such an embodiment of the test apparatus were utilized, it would be preferable to use a solid disc 34, rather than the spoked design shown in FIG. 5, to prevent the particles from falling between the spokes 124.

The carbon tape is preferably analyzed by removing the sample collection disc 34 from the apparatus 20 following the completion of a series of shock tests. The tape 150 is then removed from the disc 34 and analyzed in a conventional manner, similar to the analysis of the contents of the particle trap 146. However, the disc 34 may be rotated (either separately or together with the hub 88 as described above) following each shock event during the series of shock tests so that a relatively clean portion of the carbon tape 150 is positioned beneath the HSA 48 for each shock test. Of course, it is preferable to rotate the media disc 32 itself following each shock test so that a clean, unmarred portion of the disc 32 is positioned beneath the slider 40. Thus, it may be sufficient to rotate the sample collection disc 34 together with the media disc 32 between each shock test.

In order to remove the sample collection disc 34 (for analysis of the carbon tape 150), an investigator must first remove the clamp ring 106 and the media disc 32 from the hub 88. Of course, once the media disc 32 has been removed it too may be analyzed to aid in the determination of the shock performance of the disc drive components. Such analysis may include a microscopic investigation of the disc surface to determine the severity of the head slaps (i.e., the depth of the indentions made by the impact of the slider 40). Such post-test analysis is well known to those skilled in the art and need not be explained in detail.

As noted above, each of the LDV 140, the acoustical emission sensor 142, the particle counter 144, as well as the accelerometers 132, 134 and 136, are preferably connected to a single computer (not shown) to allow the relevant data for each shock test to be recorded. This data can be combined with an analysis of the particle trap 146 by changing the trap 146 for each shock test and identifying the trap with the relevant shock test so that the later analysis of the trap 146 can be combined with the prior test data collected by the computer. Similarly, the sample collection disc 134 can be marked before the test to provide space around the circumference of the disc 134 for each shock test within the series of tests. An investigator could then rotate the disc 134 by a predetermined amount after each shock test so that a later analysis of the carbon tape 150 could be combined with the prior test results. A similar procedure could be followed with respect to the media disc 32 itself if it is desired to perform an analysis of the disc surface at the conclusion of the test.

The procedure for using the apparatus 20 and the above described analysis equipment to conduct a shock test begins with securing the appropriate disc drive components within the apparatus 20. For instance, a HSA 48 is preferably secured to the distal end of the actuator arm 28 and a fresh media disc is attached to the hub 88 as shown in FIG. 5. Similarly, a fresh application of carbon tape 150 is applied to the sample collection disc 34 prior to securing the disc 34 to the hub 88. Next, the slider 40 is positioned at the appropriate location on the surface of the media disc 32 and the top cover 24 is sealed to the base portion 22 of the apparatus. The shock test is initiated by the application of a control signal from a controller (not shown) to the shock pulse generators 26 and 30 to provide a desired shock to the disc drive components such as the HSA 48 and the media disc 32. The accelerometers attached to these components then record the magnitude and duration of the shock for each generator 26 and 30, as well as the magnitude of the shock (if any) experienced by the apparatus 20 itself. During this shock event the LDV 140 and the acoustical emission sensor 142 measure the movement and vibration of the HSA 48 as well as the relative movement between the HSA 48 and the media disc 32. Similarly, the particle counter 144 analyzes the number of particles generated during the test by counting the particles ingested by the sniffer 156 for a predetermined period of time following the application of the shock. At the conclusion of the test, or following a series of tests, the contents of the particle trap 146 are analyzed as are the contents of the carbon tape 150 secured to the disc 34. In addition, both the disc 32 and the slider 40 may be removed from the apparatus for a visual analysis of these disc drive components. The results of all of these tests are then used in a comparative analysis to determine the relative shock performance of different disc drive components.

While the above description of the apparatus 20 and the associated test instruments describes a presently preferred embodiment of the present invention, those skilled in the art could easily modify the apparatus 20 to allow for the inclusion of additional disc drive components or the use of additional test equipment. Such modifications to the preferred embodiment of the apparatus 20 are encompassed by the present invention. For example, see FIG. 6 which illustrates a second media disc 32 secured to the hub 88. Similarly, the actuator arm 28 may be modified as described above to include a second HSA 48 so that each media disc 32 is engaged by a pair of sliders 40 as in a typical disc drive. Alternatively, other disc drive components beyond the HSA 48 and the media disc 32 may be shock tested within the apparatus 20. Additionally, the present invention encompasses the use of alternative shock pulse generators or vibrators as well as the use of only a single shock pulse generator. For example, one skilled in the art may modify the apparatus 20 to use only a single shock pulse generator to impart an impulse to one of the disc 32 or the HSA 48. While a single shock pulse generator would not provide the same degree of flexibility in simulating the types of shocks experienced by actual disc drives, a single generator would still allow for valid comparative shock testing of disc drive components such as suspensions 38, sliders 40 or media discs 32 (e.g., only a single shock pulse generator is required to generate a head slap between the slider 40 and the disc 32).

The apparatus 20 represents a vast improvement over prior art whole-drive shock testing, particularly when it is desired to evaluate the shock performance of individual disc drive components as opposed to evaluating the survivability of an assembled disc drive. The apparatus 20 allows investigators to test different disc drive components prior to assembling a disc drive, thereby reducing the time required to bring a new disc drive to market. Furthermore, the apparatus 20 provides more accurate and repeatable shock test results than the prior art whole-drive drop testers by allowing investigators to isolate the shock performance of one or two disc drive components. In essence, the apparatus 20 improves the ability of an investigator to analyze the performance of a single disc drive component without the test results being skewed by any interaction between that component and the remaining components found within a typical disc drive. Additionally, the apparatus 20 allows the use of certain analysis equipment and techniques that could not previously be used with whole-drive drop testers (e.g., the use of the LDV 140 and the sample collection disc 34 positioned below the media disc 32).

Additionally, the shock test apparatus 20 of the present invention is relatively simple to use and is much faster and efficient than prior art whole-drive shock testers that require assembly of an entire disc drive prior to testing the shock performance of a new disc drive component. Indeed, a media disc 32 and a HSA 48 can be loaded into the apparatus 20 of the present invention in a matter of minutes so that an entire battery of shock tests can be conducted at one time.

In summary, the preferred embodiment exemplary of the invention and disclosed herein is directed to an apparatus (such as 20) having a base portion (such as 22) and a detachable top cover (such as 24) defining an interior volume for securing a first disc drive component (such as 48) and a second disc drive component (such as 32 or 42) so that the two components contact one another in the absence of a shock. The apparatus includes a shock pulse generator (such as 26) that extends into the interior volume of the apparatus and which includes an actuator (such as 52) for imparting a shock pulse to the first disc drive component (such as 48) to create a dynamic interaction (e.g., a "head slap") between the first disc drive component (such as 48) and the second disc drive component (such as 32 or 42).

In another preferred embodiment of the present invention, the apparatus (such as 20) includes an actuator arm (such as 28) attached to the first disc drive component (such as 48). A support (such as 54 and 56) holds the actuator arm above the actuator (such as 52) of the shock pulse generator (such as 26), and a programmer disc (such as 64) is positioned between the actuator arm (such as 28) and the actuator (such as 52) of the shock pulse generator (such as 26) to alter the shock pulse transmitted to the first disc drive component (such as 48).

In another preferred embodiment of the present invention, the apparatus includes a second shock pulse generator (such as 30) having an actuator (such as 72) that imparts a shock pulse to the second disc drive component (such as 32).

In another preferred embodiment of the present invention, a hub (such as 88) is connected to the actuator (such as 72) of the second shock pulse generator (such as 30) to allow rotation of the hub (such as 88) relative to the actuator (such as 72). The second disc drive component (such as 32) is then attached to the hub (such as 88).

In another preferred embodiment of the present invention, a sample collection disc (such as 34) is attached to the hub (such as 88) below the second disc drive component (such as 32).

In another preferred embodiment of the present invention, the base portion (such as 22) defines an access port (such as 126 or 128) to allow rotation of the hub (such as 88) from an exterior of the apparatus (such as 20). An adhesive cover (such as 130) preferably seals the access port (such as 126 or 128).

In another preferred embodiment of the present invention, a first accelerometer (such as 132) is attached to the first disc drive component (such as 48), while a second accelerometer (such as 134) is attached to the hub (such as 88).

In another preferred embodiment of the present invention, an acoustic emission sensor (such as 142) is attached to either the first disc drive component (such as 48) or the first shock pulse generator (such as 26).

In another preferred embodiment of the present invention, a window (such as 152) is formed in the top cover (such as 24) of the apparatus and positioned over the first disc drive component (such as 48).

A further preferred embodiment of the present invention includes a system for evaluating the shock performance of individual disc drive components and includes an enclosure (such as 20) having a base portion (such as 22) and a top cover (such as 24) detachably secured together to define an interior volume for securing a first disc drive component (such as 48) and second disc drive component (such as 32 or 42) within the interior volume so that the two components contact one another in the absence of a shock. The system includes a shock pulse generator (such as 26) having an actuator (such as 52) extending into the interior volume of the enclosure (such as 20) to impart a shock pulse to the first disc drive component (such as 48) to create a dynamic interaction (e.g., a "head slap") between the first disc drive component (such as 48) and the second disc drive component (such as 32 or 42). The system further includes means (such as 132 and 136) for measuring the shock pulse imparted to the first disc drive component (such as 48) in addition to means (such as 34, 140, 142, 144 and 146) for measuring the dynamic interaction between the first disc drive component (such as 48) and the second disc drive component (such as 32 or 42).

In another preferred embodiment of the present invention, the system includes a second shock pulse generator (such as 30) having an actuator (such as 72) that imparts a shock pulse to the second disc drive component (such as 32), as well as means (such as 134) for measuring the shock pulse imparted to the second disc drive component (such as 32).

In another preferred embodiment of the present invention, a window (such as 152) is formed in the top cover (such as 24) of the enclosure (such as 20) and positioned over the first disc drive component (such as 48). The system further includes as one means for measuring the dynamic interaction between the first disc drive component (such as 48) and the second disc drive component (such as 32 or 42) a laser Doppler vibrometer (such as 140) positioned outside of the enclosure (such as 20) and above the window (such as 152).

In another preferred embodiment of the present invention, the top cover (such as 24) of the enclosure (such as 20) defines an opening for receiving a probe (such as 156). The system further includes as one means for measuring the dynamic interaction between the first disc drive component (such as 48) and the second disc drive component (such as 32 or 42) a particle counter (such as 144) connected to the probe (such as 156) to suction particles generated by the interaction between the disc drive components.

In another preferred embodiment of the present invention, the system includes a particle trap (such as 146) that is also connected to the probe (such as 156) but which functions separately from the particle counter (such as 144).

In another preferred embodiment of the present invention, the system further includes as one means for measuring the dynamic interaction between the first disc drive component (such as 48) and the second disc drive component (such as 32 or 42) an acoustical emission sensor (such as 142) attached within the enclosure (such as 20).

A further preferred embodiment of the present invention relates to system for evaluating the shock performance of a first disc drive component (such as 48) and a second disc drive component (such as 32 or 42) including means (such as 26) for imparting a shock to the first disc drive component (such as 48) to observe the shock performance of the first and second disc drive components without assembling the first and second disc drive components in a disc drive.

It is to be understood that even though numerous characteristics and advantages of various embodiments of the present invention have been set forth in the foregoing description, together with details of the structure and function of various embodiments of the invention, this disclosure is illustrative only, and changes may be made in detail, especially in matters of structure and arrangement of parts within the principles of the present invention to the full extent indicated by the broad meaning of the terms in which the appended claims are expressed.

What is claimed is:

1. A shock test apparatus for evaluating the shock performance of individual disc drive components, the apparatus comprising:
   a base portion;
   a top cover detachably secured to the base portion to define an interior volume;
   first and second disc drive components detachably secured within the interior volume of the apparatus so that the first disc drive component contacts the second disc drive component in the absence of a shock event;
   a shock pulse generator extending into the interior volume of the apparatus, the shock pulse generator having an actuator that moves vertically in relation to the generator, the actuator imparting a shock pulse to the first disc drive component to create a dynamic interaction between the first and second disc drive components; and
   means for measuring the dynamic interaction between the first and second disc drive components.

2. A shock test apparatus as defined in claim 1 wherein the first disc drive component is a head suspension assembly and the second disc drive component is a ramp for holding the head suspension assembly.

3. A shock test apparatus as defined in claim 2 further comprising:
   an actuator arm attached to a proximal end of the head suspension assembly;
   a support for holding the actuator arm above the actuator of the shock pulse generator; and
   a programmer disc positioned between the actuator arm and the actuator of the shock pulse generator, the programmer disc adapted to alter the shock pulse imparted to the head suspension assembly.

4. A shock test apparatus as defined in claim 1 wherein the first disc drive component is a head suspension assembly and the second disc drive component is a media disc that supports a slider of the head suspension assembly.

5. A shock test apparatus as defined in claim 4 further comprising:
   an actuator arm attached to a proximal end of the head suspension assembly;
   a support for holding the actuator arm above the actuator of the shock pulse generator; and
   a programmer disc positioned between the actuator arm and the actuator of the shock pulse generator, the programmer disc adapted to alter the shock pulse imparted to the head suspension assembly.

6. A shock test apparatus as defined in claim 1 further comprising:
   a second shock pulse generator extending into the interior volume of the apparatus, the second shock pulse generator having an actuator that imparts a shock pulse to the second disc drive component.

7. A shock test apparatus as defined in claim 6 wherein the first disc drive component is a head suspension assembly and the second disc drive component is a media disc that supports a slider of the head suspension assembly.

8. A shock test apparatus as defined in claim 7 further comprising:
   an actuator arm attached to a proximal end of the head suspension assembly;
   a support for holding the actuator arm above the actuator of the first aforesaid shock pulse generator; and
   a programmer disc positioned between the actuator arm and the actuator of the first shock pulse generator, the programmer disc adapted to alter the shock pulse imparted to the head suspension assembly.

9. A shock test apparatus as defined in claim 8 further comprising:
   a hub operatively attached to the actuator of the second shock pulse generator to allow rotation of the hub relative to the actuator, wherein the media disc is attached to the hub.

10. A shock test apparatus as defined in claim 9 wherein the means for measuring the dynamic interaction between the first and second disc drive components includes a sample collection disc attached to the hub below the media disc.

11. A shock test apparatus as defined in claim 10 wherein the base portion defines at least one access port to allow rotation of the hub from an exterior of the apparatus, the apparatus further comprising:
    an adhesive cover to seal the access port.

12. A shock test apparatus as defined in claim 9 wherein the means for measuring the dynamic interaction between the first and second disc drive components includes a first accelerometer attached to one of the actuator arm and the head suspension assembly and a second accelerometer attached to the hub.

13. A shock test apparatus as defined in claim 12 wherein the means for measuring the dynamic interaction between the first and second disc drive components further includes an acoustic emission sensor attached within the interior volume of the apparatus.

14. A shock test apparatus as defined in claim 12 wherein the means for measuring the dynamic interaction between the first and second disc drive components further includes an opening formed in the top cover of the apparatus and positioned over the head suspension assembly, the opening including a window formed from anti-reflective glass to allow for observation of the head suspension assembly and the media disc.

15. A system for evaluating the shock performance of individual disc drive components, the system comprising:
   an enclosure having a base portion and a top cover detachably secured together to define an interior volume of the enclosure, the enclosure securing first and second disc drive components within the interior volume so that the first disc drive component contacts the second disc drive component in the absence of a shock event;
   a shock pulse generator having an actuator extending into the interior volume of the enclosure, the actuator moving vertically to impart a shock pulse to the first disc drive component to create a dynamic interaction between the first and second disc drive components;
   means for measuring the shock pulse imparted to the first disc drive component; and
   means for measuring the dynamic interaction between the first and second disc drive components.

16. A system as defined in claim 15 further comprising:
   a second shock pulse generator having an actuator extending into the interior volume of the enclosure to impart a shock pulse to the second disc drive component; and
   means for measuring the shock pulse imparted to the second disc drive component.

17. A system as defined in claim 16 wherein the first disc drive component is a head suspension assembly and the second disc drive component is a media disc that supports a slider of the head suspension assembly.

18. A system as defined in claim 17 further comprising:
   a hub operatively attached to the actuator of the second shock pulse generator to allow rotation of the hub relative to the actuator of the second shock pulse generator, wherein the media disc is attached to the hub.

19. A system as defined in claim 18 wherein the means for measuring the shock pulses imparted to the first and second disc drive components include:
   a first accelerometer attached to the head suspension assembly; and
   a second accelerometer attached to the hub.

20. A system as defined in claim 18 wherein:
   the top cover of the enclosure defines an opening positioned over the head suspension assembly, the opening including a window formed from anti-reflective glass; and
   the means for measuring the dynamic interaction between the first and second disc drive components includes a laser Doppler vibrometer positioned outside of the enclosure and above the window.

21. A system as defined in claim 18 wherein:
   the top cover of the enclosure defines an opening for receiving a probe; and
   the means for measuring the dynamic interaction between the first and second disc drive components includes a particle counter having a probe extending through the opening defined in the enclosure, the particle counter operating to suction particles generated by the interaction between the first and second disc drive components.

22. A system as defined in claim 21 wherein the means for measuring the dynamic interaction between the first and second disc drive components further includes a particle trap operating separately from the particle counter.

23. A system as defined in claim 18 wherein:
   the means for measuring the dynamic interaction between the first and second disc drive components includes a sample collection disc attached to the hub below the media disc.

24. A system as defined in claim 18 wherein:
   the means for measuring the dynamic interaction between the first and second disc drive components includes an acoustical emission sensor attached within the interior volume of the enclosure.

* * * * *